(12) United States Patent
Weiss et al.

(10) Patent No.: US 8,447,416 B2
(45) Date of Patent: May 21, 2013

(54) FIELD DECOUPLING ELEMENT FOR USE WITH AN IMPLANTABLE LINE AND IMPLANTABLE MEDICAL DEVICE

(75) Inventors: Ingo Weiss, Berlin (DE); Stefan Knorr, Berlin (DE); Michelle Maxfield, Berlin (DE); Michael Friedrich, Kleinmachnow (DE)

(73) Assignee: Biotronik CRM Patent AG, Baar (CH)

( * ) Notice: Subject to any disclaimer, the term of this patent is extended or adjusted under 35 U.S.C. 154(b) by 982 days.

(21) Appl. No.: 12/422,052

(22) Filed: Apr. 10, 2009

(65) Prior Publication Data
US 2010/0099281 A1 Apr. 22, 2010

(30) Foreign Application Priority Data
Apr. 14, 2008 (DE) .......... 10 2008 018 992

(51) Int. Cl.
*A61N 1/05* (2006.01)
*A61N 1/372* (2006.01)
*H01R 4/58* (2006.01)

(52) U.S. Cl.
USPC .......... 607/122; 607/116; 439/86; 439/179

(58) Field of Classification Search
USPC .......... 607/122, 116, 119; 600/333
See application file for complete search history.

(56) References Cited

U.S. PATENT DOCUMENTS

| | | | |
|---|---|---|---|
| 5,372,133 A * | 12/1994 | Hogen Esch | 600/377 |
| 5,458,630 A * | 10/1995 | Hoegnelid et al. | 607/116 |
| 7,003,336 B2 * | 2/2006 | Holker et al. | 600/316 |
| 8,086,321 B2 * | 12/2011 | Ameri | 607/63 |
| 8,103,358 B2 * | 1/2012 | Sommer et al. | 607/122 |
| 2003/0032892 A1 * | 2/2003 | Erlach et al. | 600/547 |
| 2005/0222657 A1 | 10/2005 | Wahlstrand et al. | |
| 2006/0247747 A1 | 11/2006 | Olsen et al. | |
| 2006/0252314 A1 | 11/2006 | Atalar et al. | |
| 2007/0066998 A1 * | 3/2007 | Hansen et al. | 607/4 |
| 2007/0233215 A1 * | 10/2007 | Sommer et al. | 607/122 |
| 2009/0149909 A1 * | 6/2009 | Ameri | 607/37 |
| 2009/0259281 A1 * | 10/2009 | Weiss et al. | 607/116 |
| 2010/0204766 A1 * | 8/2010 | Zdeblick et al. | 607/119 |
| 2010/0249883 A1 * | 9/2010 | Zdeblick | 607/60 |

FOREIGN PATENT DOCUMENTS
WO   WO 03/037424   5/2003

OTHER PUBLICATIONS
European Search Report Dated Apr. 14, 2011 (6 pages).

* cited by examiner

*Primary Examiner* — Carl H Layno
*Assistant Examiner* — Erin Piateski
(74) *Attorney, Agent, or Firm* — Arc IP Law, PC; Joseph J. Mayo

(57) ABSTRACT

A field decoupling element for use with an implantable line with an elongated line body and a function conductor which extends in the longitudinal direction of the line body and acts to implement a medical function of the line, such that the field decoupling element is in electric contact with the function conductor in the use state connected to the line and reduces coupling of the function conductor to an external field.

7 Claims, 11 Drawing Sheets

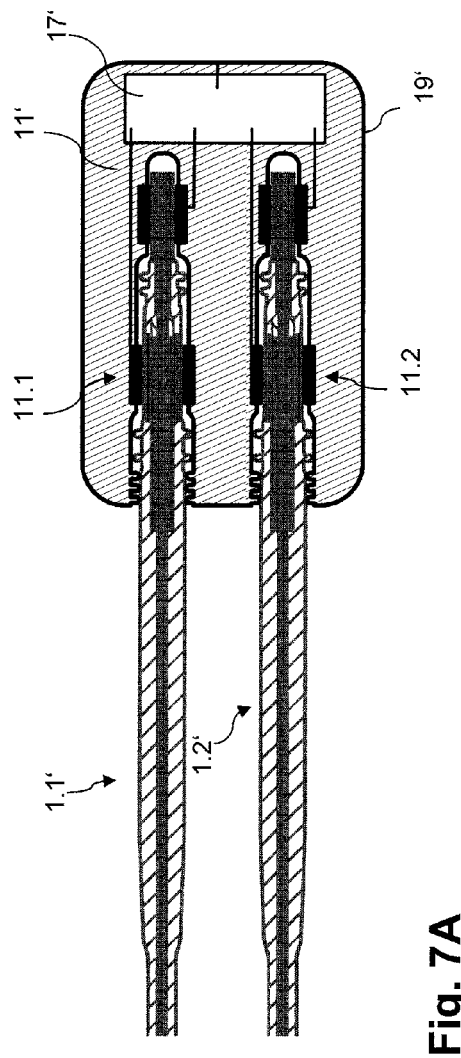
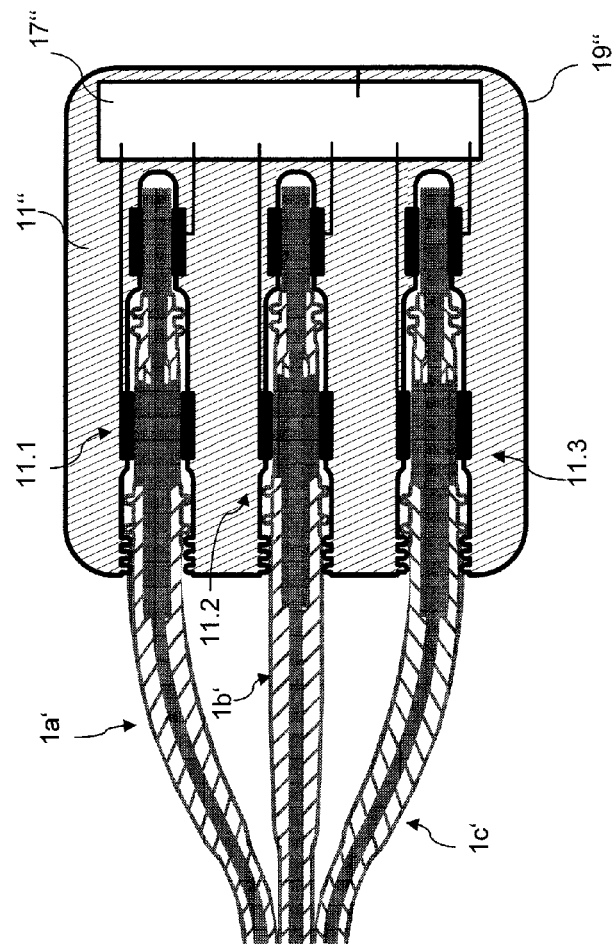
Fig. 7A
Fig. 7B

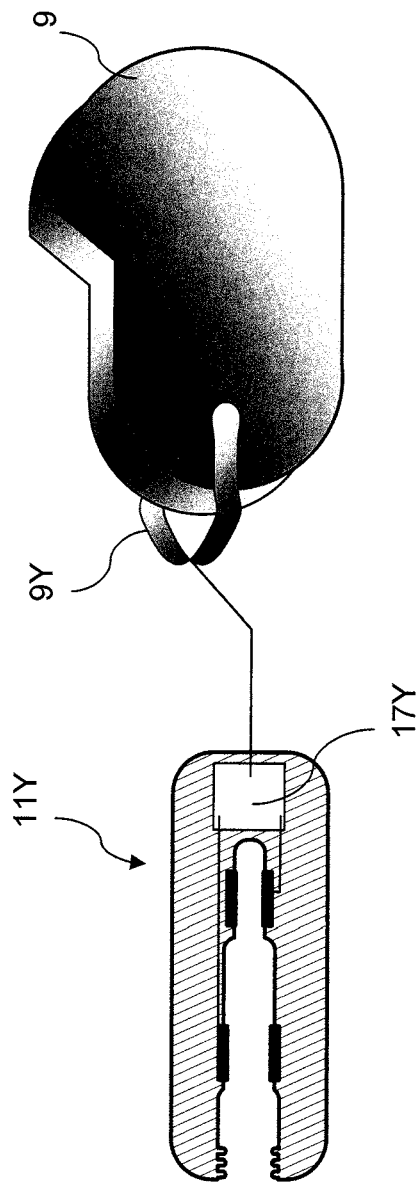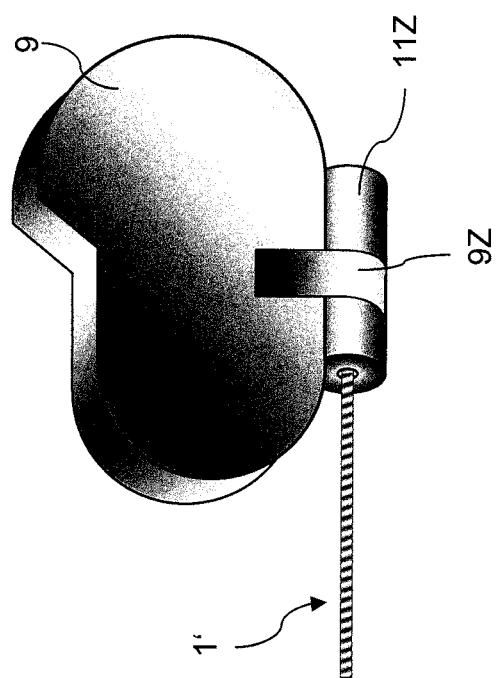
Fig. 11A
Fig. 11B

2

FIELD DECOUPLING ELEMENT FOR USE WITH AN IMPLANTABLE LINE AND IMPLANTABLE MEDICAL DEVICE

This application takes priority from German Patent Application DE 10 2008 018 992.8, filed 14 Apr. 2008, the specification of which is hereby incorporated herein by reference.

BACKGROUND OF THE INVENTION

1. Field of the Invention

The invention relates to a field decoupling element for use with an implantable line having an elongated line body and a function conductor extending in the longitudinal direction of the line body, acting to implement a medical function of the line. The invention also relates to an implantable line of the aforementioned type as well as an implantable medical device for connection of such an implantable line.

2. Description of the Related Art

Medical implants such as pacemakers and defibrillators often have an electric connection to the interior of a patient's body. Such a connection serves to measure electric signals and/or to stimulate cells in the body. This connection is often embodied as an elongated electrode. At the present time, electric signals are transmitted between the implant and the electrode contacts, such as, but not limited to, tips, rings, HV shock coils and sensors with materials that are good conductors.

If an implant-and-electrode system is exposed to strong interfering fields (EMI, MRI), an unwanted malfunction may occur, specifically heating of parts of the system or electric malfunctions (e.g., resets). The heating may result in damage to body tissue or organs when the heated parts come in direct contact with the tissue. This is the case with the electrode tip in particular.

The cause of the unwanted malfunction is the interaction of the field with the elongated line structure of the electrode. The electrode acts like an antenna, receiving energy from the surrounding fields. This energy on the lines that are used therapeutically can be emitted by the antenna distally to the tissue via the electrode contacts (tip, ring, . . . ) or emitted proximally to the implant.

The same problems also occur with other elongated conductive structures whose proximal end is not necessarily connected to an implant (e.g., catheters, temporary electrodes).

BRIEF SUMMARY OF THE INVENTION

The object of the invention is to provide an improved implantable line of the aforementioned type which has improved properties in strong external fields.

This object is achieved by providing a field decoupling element having the features of the independent claim(s) made herein and, according to relatively independent aspects of the invention, by an implantable line having the features of independent claims made herein and finally by an implantable medical device having the features of independent claims made herein.

An essential idea of the invention consists of providing an element to be connected to or integrated into the implantable line such that this element varies the interaction of the line structure, i.e., of the function conductor(s) with external interference fields in the sense that the antenna effect of the line structure becomes worse as a result. Therefore, the proposed element is known as a field decoupling element; this term should be understood to refer not to achieving complete decoupling of the line structure from external fields but instead merely a gradual decoupling.

In the use state, the field decoupling element is in contact with at least one function conductor of the implantable line and may additionally be in contact with additional conductive elements or regions, e.g., with body fluid, skin, other implanted lines, including the housing of an implantable medical device, at a reference potential (e.g., ground), etc. Contact here is understood in general to refer to a low-impedance electric connection, which may occur due to a capacitive coupling with high-frequency signals.

In particular, a field decoupling element having at least two contacts for contacting the function conductor of the line as well as another conducting element in a patient's body and a switched-mode network connecting the two contacts. This network comprises, for example:

- discrete components: resistors, capacitors, inductors, which form an electric network,
- conducting or dielectric materials (plastics, metals, ceramics),
- sensors (thermocouples, thermistors, field strength sensors, . . . ),
- semiconductor structures,
- nonlinear components/structures,
- components a having giant magnetoresistance (GMR), anisotropic magnetoresistance (AMR), colossal magnetoresistance (CMR) or tunnel magnetoresistance (TMR), or by combinations of the aforementioned compounds.

In another embodiment of the present invention, the field decoupling element is provided with an elastic conductive section or part which, in the use state, keeps the function conductor of a connected line in permanent contact with another conducting element in a patient's body even under the influence of a mechanical force. In addition, it is possible to provide for the field decoupling element to have a section or a part of an electrically conductive plastic connecting the first contact to the second contact in particular. As an alternative to or in combination with this, it is possible for the field decoupling element to have a metallic section or a metallic part which connects the first contact to the second contact and into which an adjustable or elastic contacting element is inserted in particular.

A targeted adjustment of the mechanical and electric properties of the field decoupling element can be achieved through the choice of materials with which a wide variety of line structures can be significantly improved with regard to their performance in strong external fields and a wide variety of applications can be covered. In this sense, it is also possible to provide for a surface section comprising a highly conductive material to be covered with an insulating layer which consists in particular of such a material and/or is of dimensions such that it has a predefined low impedance.

According to another embodiment of the invention, a conductive liquid is used to mediate the desired contact between a function conductor and other implanted conducting parts. A corresponding field decoupling element in particular has a cavity connecting at least the first contact to the second contact to receive a conductive liquid which is embodied in particular in such a way that in the use state, a patient's body fluid can penetrate into it and establishes an electric connection between the contacts. In this sense, the field decoupling element is thus completed structurally and functionally in the use state by the penetration of body fluid.

In another embodiment of the invention, the field decoupling element is designed for connection to multiple lines and/or multiple implantable medical devices. In this embodiment, it may constitute an especially simple and useful addition to, for example, a pacemaker arrangement with lines for atrial and ventricular stimulation or a combined heart pacemaker/defibrillator or other combination devices.

The proposed field decoupling element, which may also be referred to as a "proximal electrode termination" with reference to the recently popularized term "electrode" for implantable electrode lines and with reference to its usual implantation site, may have a variety of beneficial aspects in various embodiments. It may be in particular an electrode termination which is implantable;

whose components are partially or completely biocompatible;

whereby the termination connects the body tissue to at least one of the electric terminals of an electrode plug (e.g., IS1, IS4, DF1) by way of an electric network;

whereby the termination is in contact with all the terminals of an electrode and additionally is in contact with the surrounding body tissue;

whereby the electric connection to the body tissue is not galvanic but instead is capacitive;

whereby the termination fits on at least one of the standard electrode terminals (IS1, IS4, DF1);

whereby the contact between the termination and the electrode plug is ensured by a flexible substructure (e.g., lamellae or springs) of the termination and/or by a screw connection;

whereby the termination may accommodate multiple electrode plugs, which may belong to different electrodes (ICD or multiple bipolar electrodes);

which have a highly conductive contact with the surrounding tissue, e.g., can be established by a metal, a conductive plastic, a plastic with conductive particles above the percolation threshold or other substances;

which consists of a plastic having a low impedance, connecting multiple inputs of the termination, optionally being, e.g., silicone or polyurethane, optionally filled with different conductive materials, e.g., carbon, carbon black, fullerene, nanotubes, metal dust, barium titanate, aluminum, tungsten, gold, magnesium, tantalum, . . . );

whereby the impedance of the plastic depends on the frequency;

which consists at least partially of a soft elastic plastic;

which has a metallic housing;

whose highly conductive surface is partially or completely insulated, whereby the insulation may be designed so that the impedance is very low (e.g., due to an especially thin insulation);

which has no galvanic connection with body tissue, i.e., whereby the coupling to the body tissue is only capacitive;

whereby some of the electric inputs (tissue, line(s) of the $1^{st}$ electrode, line(s) of the $2^{nd}$ electrode, . . . ) may be joined to one another by a low impedance, e.g., as a low-resistance or capacitive structure;

whereby the electric connection is ensured by a conductive liquid;

whereby the electric connection is ensured by body fluid;

whereby the termination has openings which allow direct contact between the electrode terminals and the body tissue;

whose electrode terminal (IS1, IS4, DF1) has another terminal for a conductor (MRIwire) placed in the interior lumen of the electrode in addition to the usual contacts, such that the reliable electric contact with this conductor can be ensured by a resilient structure;

whereby the termination is an active implant (pacemaker, ICD, stimulator, . . . );

whereby the outer shape of the termination on the proximal end is shaped so that it can injure the surrounding tissue;

whereby the termination is also in contact with an electric line structure that fits into the interior lumen of the electrode;

whereby the termination is fixedly connected to an electric line structure that fits into the interior lumen of the electrode;

whereby the termination not only has terminals for electrodes but also has another terminal for contacting another termination (e.g., of another active implant);

whereby the termination not only has terminals (bushings) for electrodes but also has at least one other electrode plug and/or other contact options for another implant (e.g., housing contact);

which may be fixedly connected to another termination (e.g., ICD), so that the position between the electrode at the termination and e.g., an ICD can be defined and the influence of the electrode on the function of the ICD can be kept constant over time;

which has terminals for multiple electrodes, at least one of which is not used for therapeutic purposes (e.g., a pacemaker to which an electrode that is no longer being used can be connected);

which can be attached to shortened electrodes;

which is not attached to the end or the shortened end of an electrode but instead is mounted along the electrode;

which has an elongated shape, so that good contact (galvanic, capacitive) with the surrounding body tissue can be established;

which has an elongated shape and after assembly is arranged mainly around the electrode (such as a tube that can be pushed over the electrode).

The invention facilitates the implementation of implantable lines and on the whole implantable medical systems and specifically electronic medical systems of the aforementioned type having improved interference field properties whose electrodes and/or tissue contacts heat up only weakly, especially in strong external fields (e.g., in an MRI examination). In one embodiment of the invention, the subsequent retrofitting of lines implanted previously is made possible by a relatively simple procedure in order to impart to them the aforementioned improved properties.

BRIEF DESCRIPTION OF THE DRAWINGS

Advantages and expediencies of the invention are also derived from the following description of exemplary embodiments on the basis of the figures.

Wherein:

FIGS. 11A and 11B show basic diagrams of another embodiment of the invention from two different aspects.

DETAILED DESCRIPTION OF THE INVENTION

Figure 1A:
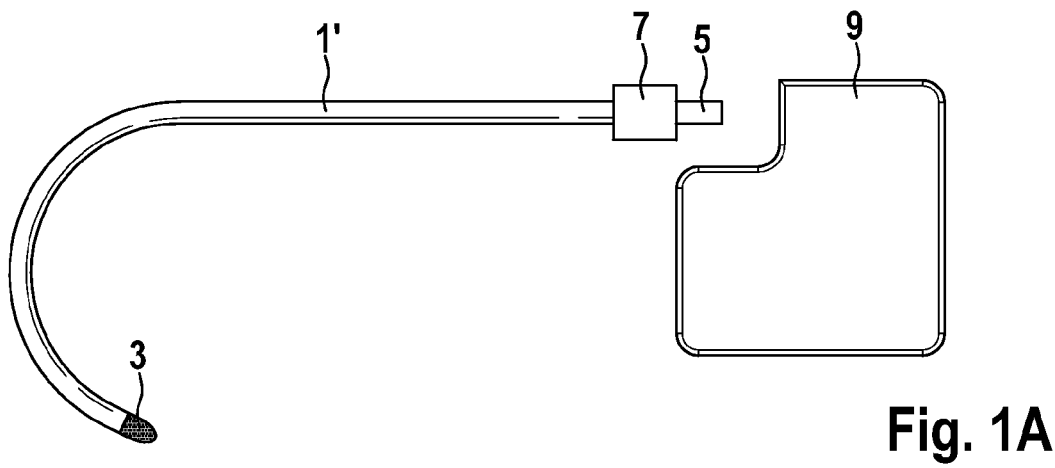
FIGS. 1A to 1C show basic diagrams of various fundamental possible embodiments of the invention.
Figure 1B:
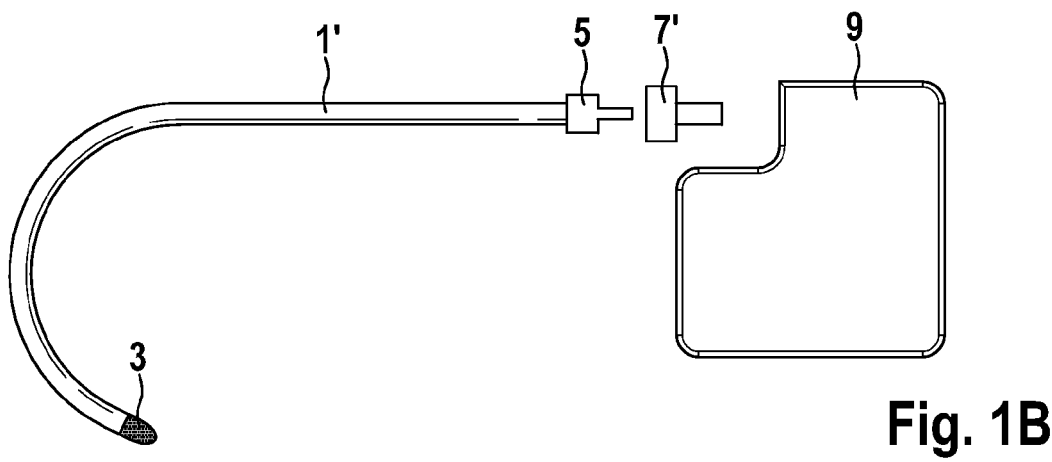
Figure 1C:
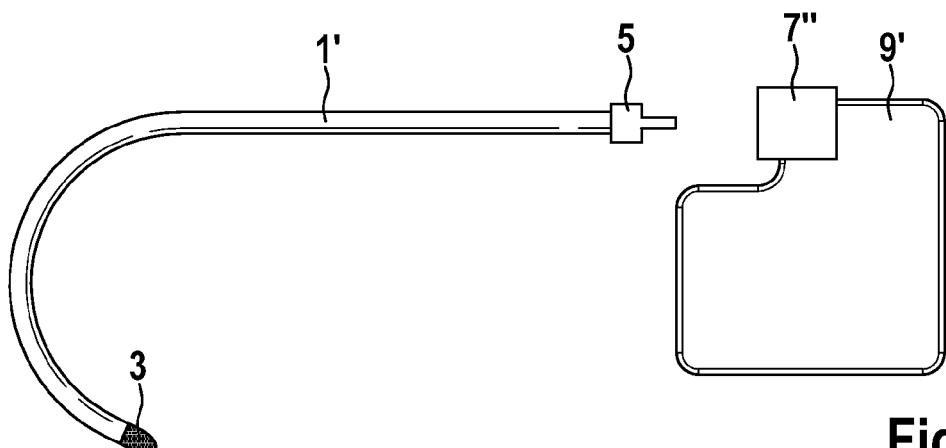

FIG. 1A shows schematically an implantable stimulation electrode line 1' having a tip electrode 3 and a proximal electrode terminal contact 5, which comprises an integrated field decoupling element 7 on the proximal end for connection to a traditional heart pacemaker 9. FIG. 1B shows another embodiment of the invention in which a separate field decoupling element 7' is provided for subsequent attachment to a traditional stimulation electrode line 1' having a tip electrode 3 and electrode terminal contact, whereby in the connection of the line to the heart pacemaker 9, the field decoupling element is inserted between the electrode terminal contact 5 and a header (not labeled separately) of the heart pacemaker. Finally, FIG. 1C shows a third possible embodiment in which the traditional stimulation electrode line 1' is connected to a modified heart pacemaker 9' into whose terminal area a suitably designed field decoupling element 7" is inserted.

Figure 2:
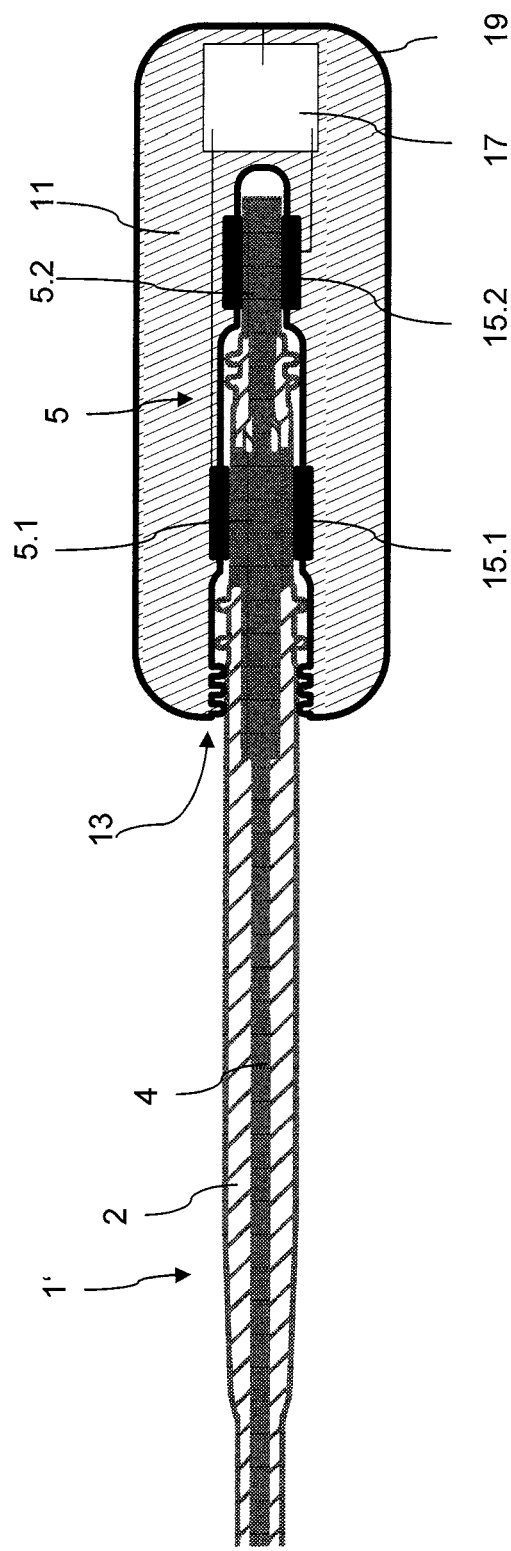
FIG. 2 shows a schematic diagram of the proximal end of an implantable line inserted into a jack of an implantable medical device and equipped with a field decoupling element.

In a simplified diagram (which does not show the presence of multiple electrode feeder lines, for example), FIG. 2 shows the proximal end section of a traditional stimulation electrode line 1' with a line body 2, a function conductor 4 and a plug section 5 having first and second electrode terminal contacts 5.1 and 5.2, inserted into a terminal bushing 11 of an electronic medical device having a plug receptacle socket 13 and first and second jack contacts 15.1 and 15.2. The jack contacts 15.1 and 15.2 are connected to one another via a field decoupling element 17, shown here symbolically, and to a conductive housing 19. The field decoupling element contains in particular a switched-mode network (not shown) of the type indicated above.

Figure 3A:
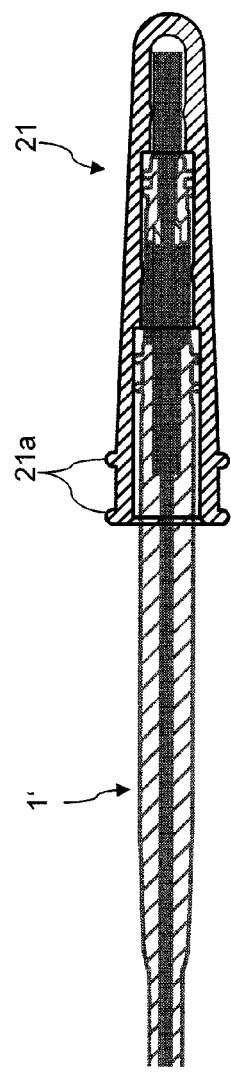
FIGS. 3A to 3C show schematic longitudinal diagrams of the proximal ends of implantable lines with different embodiments of a field decoupling element.
Figure 3B:
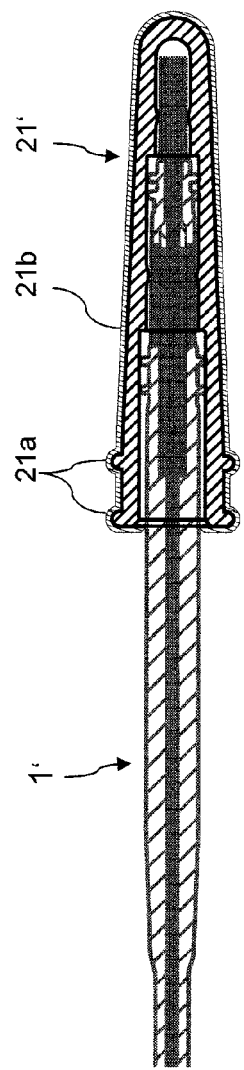
Figure 3C:
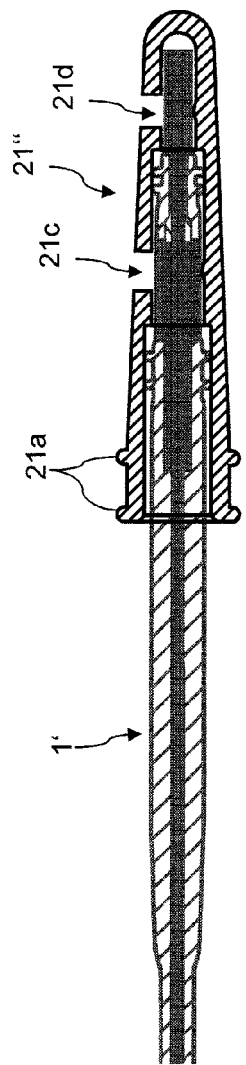
Figure 4:
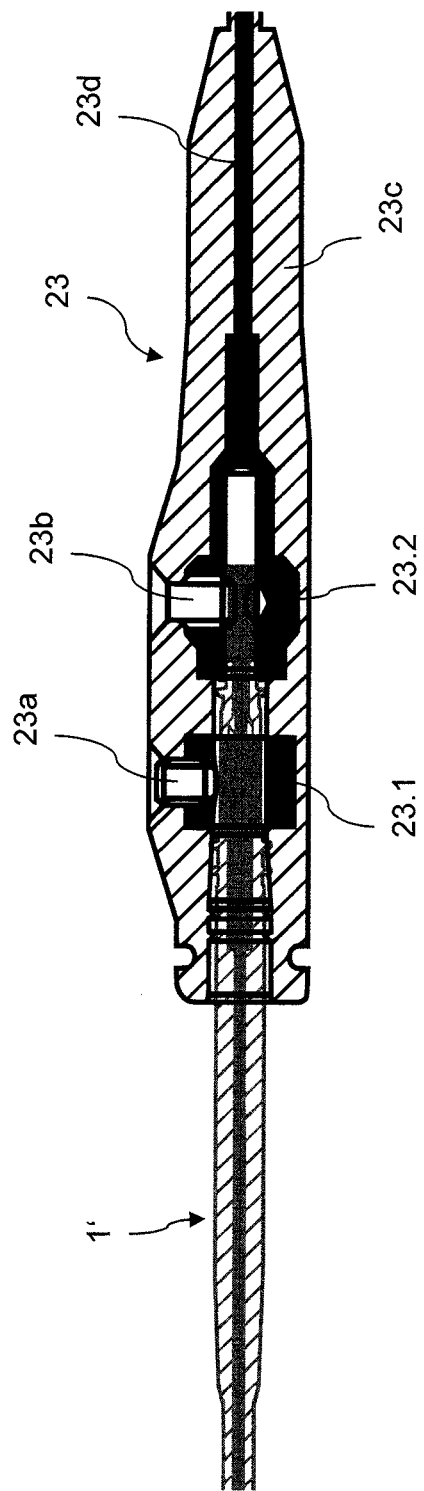
FIG. 4 shows a schematic longitudinal diagram of another embodiment of the invention.

FIGS. 3A to 3C show related embodiments of a field decoupling element 21 and/or 21' and/or 21", also labeled here as the proximal electrode termination, attached to the stimulation electrode line 1' which is already shown in FIG. 2 and whose structure is not labeled more specifically in FIGS. 3A to 3C. The field decoupling element here essentially has an elongated plastic cap, which is approximately in the shape of a truncated cone and has sealing rings 21a on its distal end. The cap has an interior space which is graduated in diameter in adaptation to the electrode terminal contacts of the line 1' and which is in electric contact with both electrode terminal contacts, joining them to one another and to the surrounding body tissue with a low resistance.

The embodiment according to FIG. 3B differs from that according to FIG. 3A by the fact that an outer insulating layer 21b is additionally provided, allowing an adjustment of the impedance with respect to surrounding body tissue regardless of the volume conductivity of the plastic material of the cap. The field decoupling element (the cap) 21" according to FIG. 3C has recesses 21c and 21d, which allow direct access of body fluid to the electrode terminal contacts of the electrode plug in the implanted state of the arrangement. Body fluid thereby becomes part of the switched-mode network connecting the line terminals in the body tissue and thereby also connecting them to one another with a relatively low impedance. A suitable design embodiment of the cap 21" ensures that no body fluid can enter the interior lumen of the electrode line. In this embodiment, the plastic material of the cap need not necessarily be conductive.

As another embodiment of the field decoupling element, again in combination with the stimulation electrode line 1' in FIGS. 2 to 3C, FIG. 4 shows a termination piece 23 having first and a second jack contacts 23.1, 23.2, each being assigned a locking screw 23a and 23b, respectively, in a plastic body 23c. The plastic body 23c also contains a connecting cable 23d running in the longitudinal direction and leading to a switched-mode network (not shown) of the field decoupling element.

As shown schematically in FIG. 5, the field decoupling element may also be used as an intermediate piece in the course of an electrode line 1 (multi-stranded here). The intermediate piece 25 in this embodiment is at the same time a branching element for branching into an additional electrode line 1.1, e.g., unused). The terminals and/or of the intermediate piece 25 may be standard terminals (IS1, IS4, HV1) or special terminals (labeled here as IS1+, IS4+, HV1+) which additionally allow connection of another line structure in the interior lumen of the electrode line 1 (optionally also serving the goal of interference field decoupling).

Figure 5A:
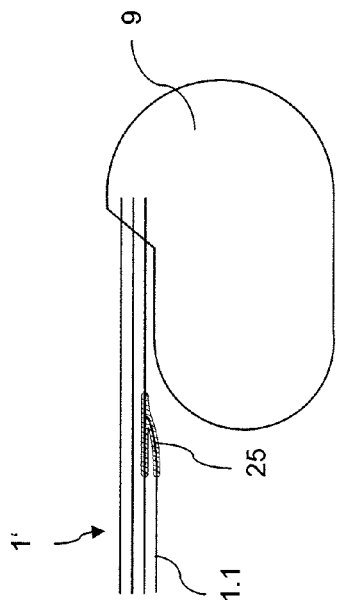
FIGS. 5A to 5C show basic diagrams of other possible embodiments of the invention.
Figure 5B:
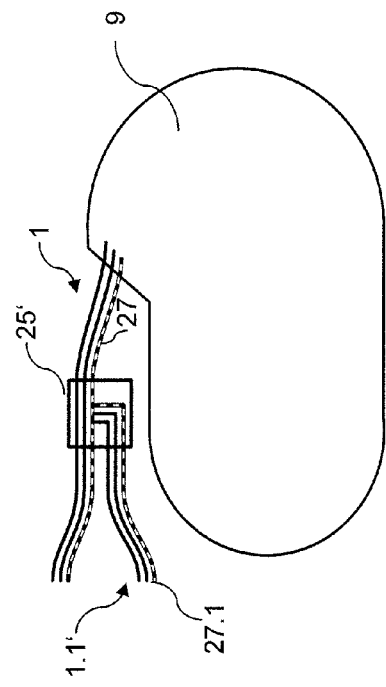

FIG. 5B shows a modification of the embodiment according to FIG. 5A, in which two bipolar electrode lines 1 and/or 1.1' are wired together across a modified intermediate piece 25'. In this embodiment, each of the two electrode lines has an additional integrated elongated field decoupling conductor 27 and/or 27.1, which is not medically active, and the intermediate piece 25' also connects these two field decoupling conductors.

Figure 5C:
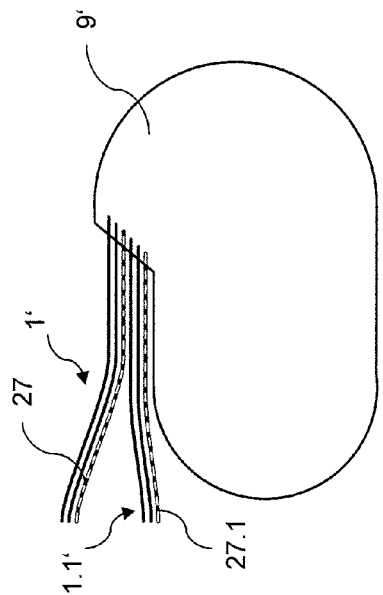

FIG. 5C shows an embodiment in which a so-called active implant (implanted electronic medical device) 9' assumes the role of the field decoupling element and/or of the proximal termination of the lines 1' and 1.1'. Here again, the two lines have an additional integrated elongated field decoupling conductor 27 and/or 27.1. Unused electrode lines can also be connected to the electronic system of the device 9', so that the switched-mode network (not shown) can be influenced actively by this electronic system for field decoupling. In this way, the switched-mode network can be controlled in a certain manner via a control intervention measure by telemetry if it can be foreseen that the patient will be entering the exposure range of a strong external field, e.g., before an MRI examination.

Figure 6:
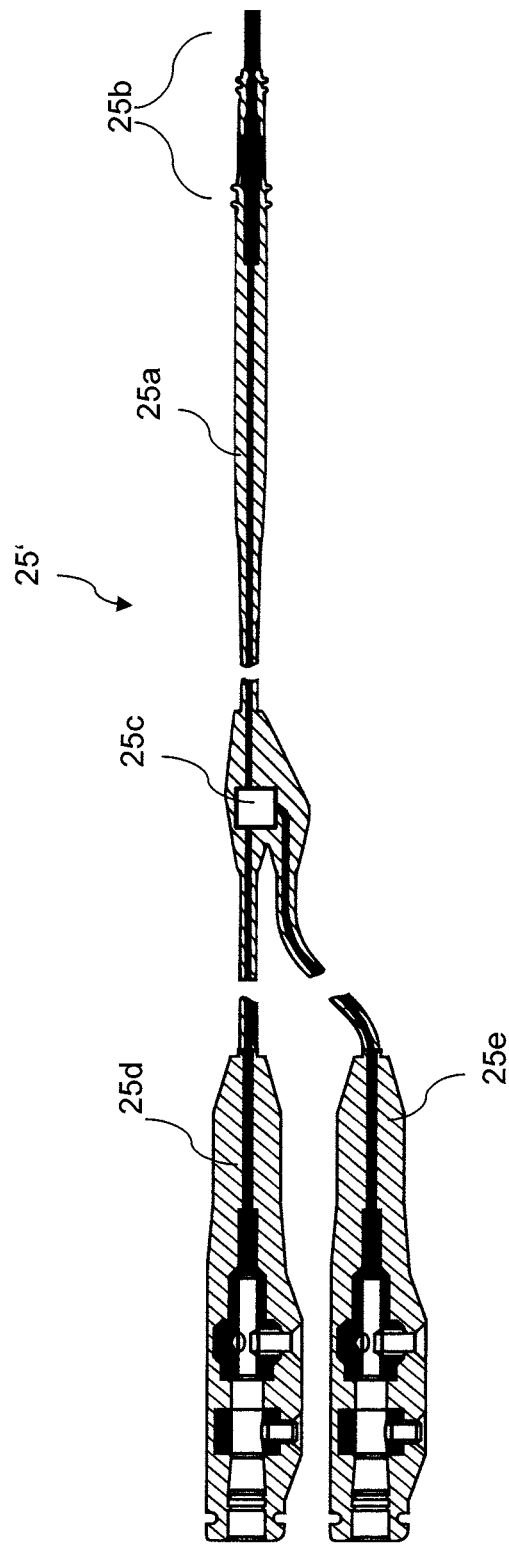
FIG. 6 shows a schematic longitudinal sectional diagram of a branched implantable line for implementation of the embodiment diagrammed schematically in FIG. 5A, FIGS. 7A and 7B show modifications of the embodiment illustrated in FIG. 2 for connection of multiple electrode lines or a multipolar electrode line.

FIG. 6 shows a mechanical embodiment of such a branch 25' according to FIG. 5B as a plastic branched line body 25a comprising a dual-pole plug section 25b on one end (proximal), a switched-mode network 25c in the branching area and two essentially similarly embodied, integrally molded jack sections 25d, 25e on the opposite end.

FIGS. 7A and 7B show modifications of the embodiments according to FIG. 2, in which two and/or three bushing sections 11.1, 11.2 and/or 11.1 through 11.3 are provided for connection of two electrode lines 1.1' and 1.2' and/or three branches 1a', 1b' and 1c' in a modified jack part 11' and/or 11" whose contact sections are each joined together by a switched-mode network 17' and/or 17" and are joined to a housing 19' and/or 19". The jack sections of the embodiment according to FIG. 7B need not be situated in one plane but instead may have a spatial configuration and they may also be embodied in different structures.

The termination does not rely on the presence of standardized electrode plugs. Terminations plugged onto electrode feeder lines are also show conceivable. For example, unused electrodes may be shortened and then provided with a termination. They then establish contact with the various lines (coil, cable, MRIwire, . . . ) of the shortened electrode, connecting the latter to an electric network and optionally also to the body.

FIGS. 8A to 8D show various possible embodiments of bipolar coiled electrode feeder lines. The lines are contacted by conductive structures at the right side of each coiled line, which are attached proximally to the electrode.

Figure 8A:
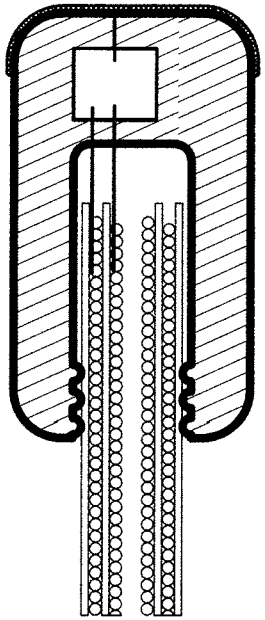
FIGS. 8A to 8D show basic diagrams of other possible embodiments of the invention.
Figure 8B:
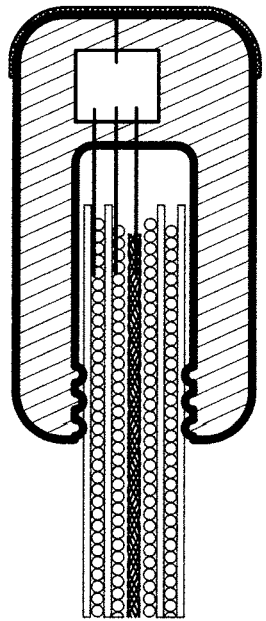
Figure 8C:
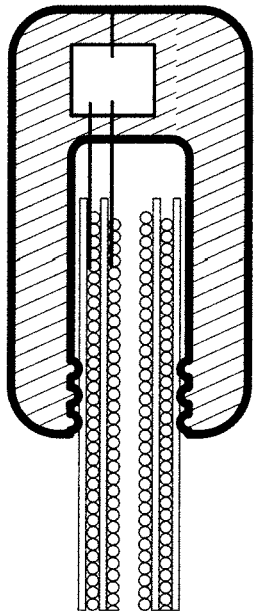
Figure 8D:
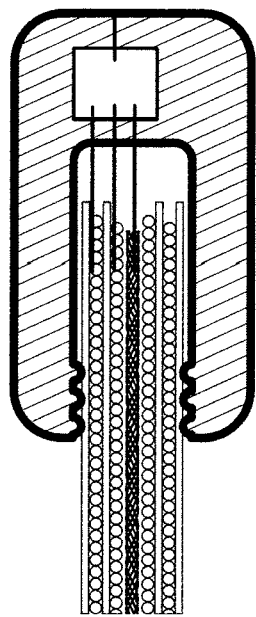

The variants according to FIGS. 8C and 8D additionally have in the interior lumen a field decoupling conductor, which is also contacted by the termination that couples to the switched-mode network shown as a square (see also FIGS. 7A-B). The versions according to FIGS. 8B and 8D differ from those in FIGS. 8A and 8C in that the housing surface is not conductive overall but only at a few locations (shown as the applied layer on the rightmost portion of the housing as a thicker line).

The electric connection to the body need not be accomplished galvanically but instead may be accomplished capacitively through a thin insulation tubing. This is true of terminations in general. Contact with the conductors may also be accomplished through screw-type structures, which are screwed into the coiled feeder lines, for example.

Figure 9A:
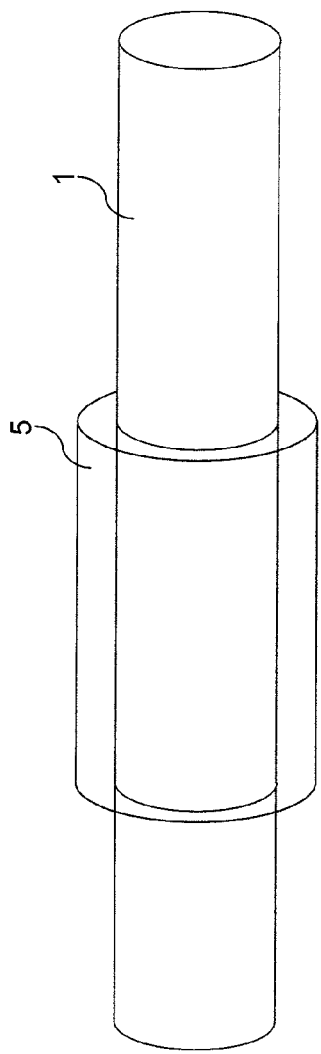
FIGS. 9A to 9C show a diagram of a perspective view and/or schematic longitudinal sectional diagrams of another fundamental possible embodiment of the invention.

The termination need not necessarily be installed at the end of an electrode. As represented symbolically in FIG. 9A, it may also be installed along an electrode (like a ferrite with an ordinary electric signal line).

Figure 9B:
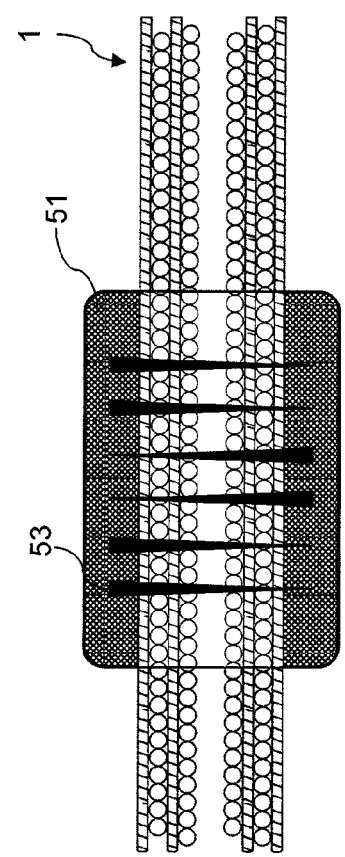
Figure 9C:
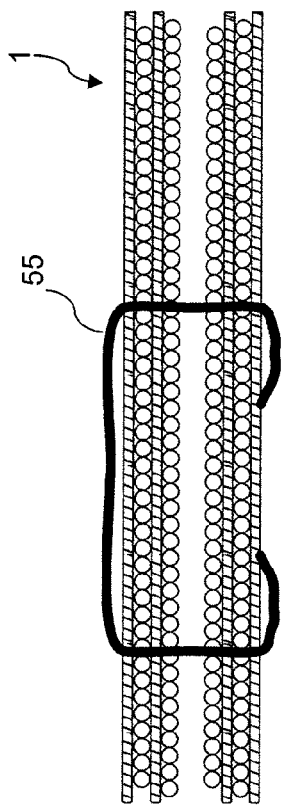

The sectional diagram of such a termination in a bipolar coiled electrode feeder line is shown in FIG. 9B. A base body 51 extends around the electrode 1. It contains multiple conductive structures 53 which join the two feeder lines together within the electrode. Together with the conductive base body, a low-resistance connection is established between the electrode feeder lines and a patient's body. Alternatively, as shown in FIG. 9C, contact between the patient's body tissue and the two electrode feeder lines may be mediated with an elongated conductive structure. The figure shows a wire, shaped into a bracket 55 and thereby connects two electrode feeder lines to the body tissue. The wire should be made of a biocompatible material. The conductive structures for contacting may also be designed so that they contact one of the two electrode feeder lines in a targeted manner and connect them to one another via a network and optionally connect them to the body. The basic body need not be conductive.

Figure 10:
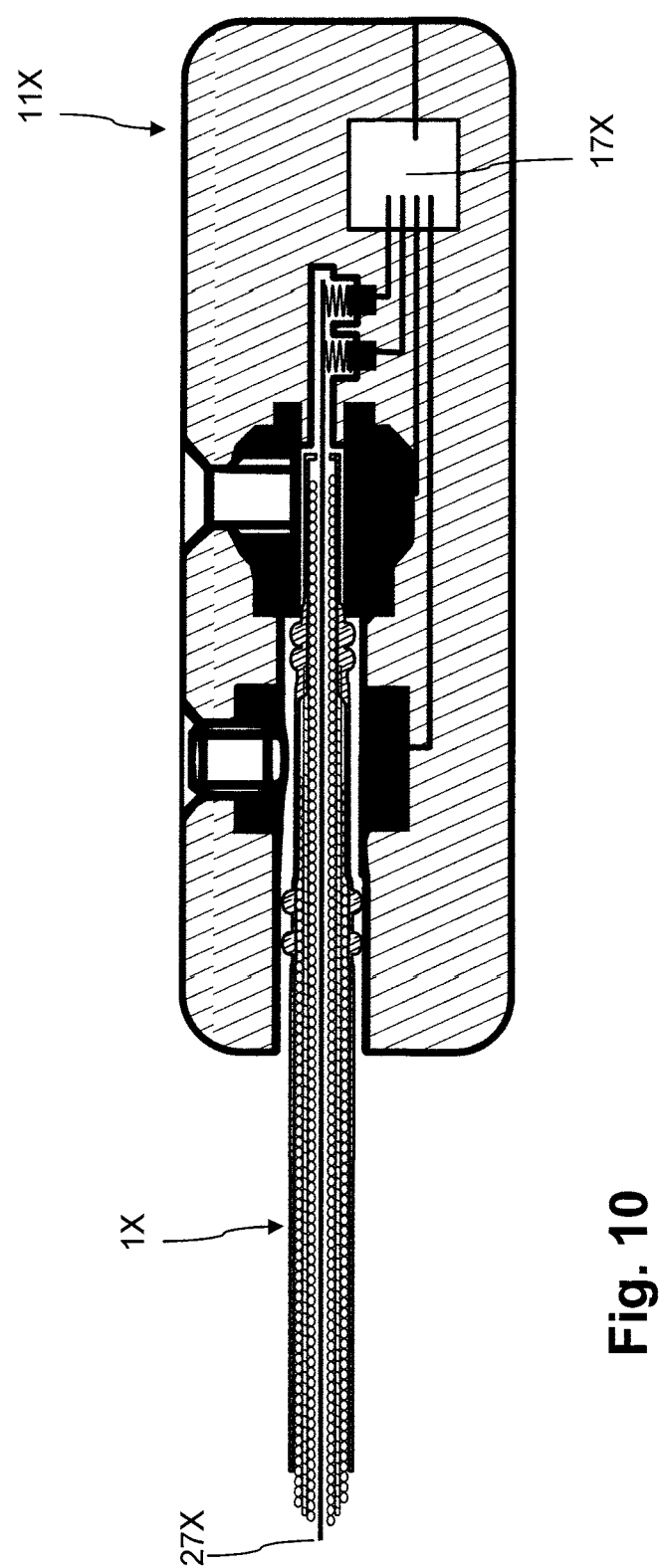
FIG. 10 shows a schematic diagram of the internal design of a heart pacemaker header having a structure according to an embodiment of the present invention.

The terminal of additional field decoupling conductors in electrode lines to a termination may be accomplished in various ways. FIG. 10 shows a termination 11X with an IS1+ terminal, which additionally contacts a two-stranded field decoupling conductor 27X and connects all the individual feeder lines of the line 1X to one another via a network 17X. The line 1X is shown as a coiled bipolar line.

It is also possible to connect the termination not only to another implant via an electrode terminal. For example, a termination may also be connected to the housing of another implant via a conductive structure. FIG. 11A shows such a structure as an example. Termination 11Y contains an electric network 17Y, whose one input is electrically connected to the housing of another implant 9. The housing contact is ensured via a bracket 9Y.

With such a construction, the termination itself need not have a conductive surface, which is galvanically or capacitively connected to the body tissue. Contact with the body tissue is ensured via the housing of the second implant.

In addition to the electric connection of a termination to another implant, the mechanical connection is also meaningful. The position of the two implants relative to one another can thus be defined in this way. A direct connection of the two implants is possible or a connection which specifies a certain distance between the two or a flexible connection (e.g., with a cable) which ensures a maximum distance between the two implants that is not to be exceeded. The restriction on the degrees of freedom of the two implants may be advantageous especially in defibrillation (internal or external). FIG. 11B shows a cylindrical termination with an electrode which is connected directly to another implant 9 via a fastening element 9Z.

This embodiment of the invention is not limited to the examples described above and the aspects of the invention emphasized above but instead is also possible in a variety of modifications which are within the scope of technical expertise.

What is claimed is:

1. A field decoupling element (7, 7', 7") comprising:
   said field decoupling element configured to couple a first end of an implantable line (1') to an implantable medical device wherein the implantable line comprises an elongated line body (2) and wherein the implantable line further comprises a function conductor (4) which extends in a longitudinal direction of the elongated line body and wherein the function conductor implements a medical function of the implantable line at least at a second end of the implantable line on an opposite end of said first end;
   said field decoupling element in electric contact with the function conductor (4) in a use state;
   wherein said field decoupling element reduces coupling of the function conductor (4) to an external field;
   at least two contacts (15.1, 15.2) within said field decoupling element wherein said at least two contacts are configured to contact the function conductor of the implantable line as well as another conductive element in a patient's body;
   a switched-mode network that connects the at least two contacts;
   a cavity within said field decoupling element that connects at least a first contact to a second contact selected from the at least two contacts and wherein the cavity is configured to receive a conductive liquid, which is formed so that in the use state, body fluid from the patient's body can penetrate and establish an electric connection between the at least said first contact and said second contact.

2. The field decoupling element (7, 7', 7") according to claim 1, wherein the switched-mode network comprises:
   at least one discrete passive component and/or
   linear component and/or
   semiconductor component and/or
   element of a dielectric material and/or
   a sensor and/or
   a component having a giant magnetoresistance, anisotropic magnetoresistance, colossal magneto-resistance effect or tunnel magnetoresistance.

3. The field decoupling element (7, 7', 7") according to claim 1, comprising:
   an elastic conductive section or part, which in the use state, holds the function conductor in a connected line in permanent contact with another conducting element in a patient's body even under an influence of mechanical force.

4. The field decoupling element (7, 7', 7") according to claim 1, comprising:
   a section or a part of an electrically conductive plastic that connects the at least two contacts.

5. The field decoupling element (7, 7', 7") according to claim 1, comprising:
   a metallic section or a metallic part such that the field decoupling element connects the at least two contacts and into which an adjustable or elastic contacting element is inserted.

6. The field decoupling element (7, 7', 7") according to claim 1, wherein a surface section of the field decoupling element is made of a highly conductive material and is covered with an insulation layer, which is made of such a material and/or is of such dimensions that it has a predetermined low impedance.

7. The field decoupling element (7, 7', 7") according to claim 1, wherein the field decoupling element is configured to connect to multiple lines and/or multiple implantable medical devices.

* * * * *